United States Patent
Kwon et al.

(10) Patent No.: US 8,266,944 B2
(45) Date of Patent: Sep. 18, 2012

(54) METHOD FOR EVALUATING SCRATCH RESISTANCE OF PLASTIC RESINS

(75) Inventors: Kee Hae Kwon, Gunpo-si (KR); Il Jin Kim, Gunpo-si (KR); Hyung Rang Moon, Seoul (KR); Jae Bum Park, Incheon (KR); Seong Ho Kong, Seoul (KR); O Sung Kwon, Gunpo-si (KR)

(73) Assignee: Cheil Industries Inc., Gumi-si (KR)

( * ) Notice: Subject to any disclaimer, the term of this patent is extended or adjusted under 35 U.S.C. 154(b) by 441 days.

(21) Appl. No.: 12/478,811

(22) Filed: Jun. 5, 2009

(65) Prior Publication Data

US 2009/0293585 A1      Dec. 3, 2009

Related U.S. Application Data

(63) Continuation-in-part of application No. PCT/KR2007/006986, filed on Dec. 28, 2007.

(30) Foreign Application Priority Data

Dec. 28, 2006    (KR) ............................. 2006-0137061

(51) Int. Cl.
*G01N 3/56* (2006.01)
(52) U.S. Cl. ............................................. 73/7
(58) Field of Classification Search .................. 73/7
See application file for complete search history.

(56) References Cited

U.S. PATENT DOCUMENTS

| | | | | |
|---|---|---|---|---|
| 2,311,430 A * | 2/1943 | Beno | ..................... | 73/7 |
| 4,472,961 A * | 9/1984 | Rehfeld et al. | ..................... | 73/7 |
| 4,791,807 A * | 12/1988 | Oechsle | ..................... | 73/78 |
| 5,359,879 A * | 11/1994 | Oliver et al. | ..................... | 73/7 |
| 5,508,517 A * | 4/1996 | Onuki et al. | ..................... | 850/6 |
| 6,502,455 B1 * | 1/2003 | Gitis et al. | ..................... | 73/150 A |
| 6,520,004 B1 * | 2/2003 | Lin | ..................... | 73/81 |
| 6,945,097 B2 * | 9/2005 | Jardret et al. | ..................... | 73/81 |
| 7,289,202 B2 * | 10/2007 | Groess et al. | ............... | 356/239.2 |
| 7,765,607 B2 * | 7/2010 | Faris | ..................... | 850/60 |
| 2006/0150710 A1 * | 7/2006 | Moyse et al. | ..................... | 73/7 |

FOREIGN PATENT DOCUMENTS

| | | |
|---|---|---|
| JP | 07-270295 A | 10/1995 |
| JP | 2001-91445 A | 4/2001 |
| KR | 10-2005-0095674 A | 9/2005 |
| WO | 2008/082218 A1 | 7/2008 |

OTHER PUBLICATIONS

International Search Report and Written Opinion for counterpart International Application No. PCT/KR2007/006986, mailed on Jan. 30, 2008.

* cited by examiner

*Primary Examiner* — Lisa Caputo
*Assistant Examiner* — Octavia Davis-Hollington
(74) *Attorney, Agent, or Firm* — Summa, Additon & Ashe, P.A.

(57) ABSTRACT

Disclosed herein is a method for evaluating scratch resistance of a plastic resin comprising scratching a surface of a test sample of plastic resin using a scratch apparatus to form a scratch of the surface having a scratch profile; scanning the scratched test sample with a surface profile analysis apparatus to measure the scratch profile; and creating a scratch resistance evaluation index based on the measured scratch profile to evaluate the scratch resistance of the test sample. The method has good reliability and reproducibility, reduces measurement time and errors caused by measurers and measuring conditions, provides easy measurement and can be widely applied to all plastic resins.

8 Claims, 5 Drawing Sheets

METHOD FOR EVALUATING SCRATCH RESISTANCE OF PLASTIC RESINS

CROSS-REFERENCE TO RELATED APPLICATIONS

This non-provisional application is a continuation-in-part application of PCT Application No. PCT/KR2007/006986, filed Dec. 28, 2007, pending, which designates the U.S. and which is hereby incorporated by reference in its entirety, and claims priority therefrom under 35 USC Section 120. This application also claims priority under 35 USC Section 119 from Korean Patent Application No. 10-2006-0137061, filed Dec. 28, 2006, the entire disclosure of which is also hereby incorporated by reference.

FIELD OF THE INVENTION

The present invention relates to a method for evaluating scratch resistance of a plastic resin.

BACKGROUND OF THE INVENTION

Commercially used plastic resins are lighter than glasses and have good physical properties such as moldability and impact resistance. The surfaces of many plastic resins, however, have poor scratch resistance. In order to improve the scratch resistance of plastic resins, a hard coating method has been widely used. The hard coating method includes the steps of coating a surface of an injection-molded resin with an organic-inorganic hybrid material and curing the organic-inorganic hybrid material using ultraviolet radiation. The additional coating process step, however, increases processing times and manufacturing costs and raises environmental concerns.

There is an increased need for non-coated resin products in view of the environmental problems and manufacturing costs associated with the production of coated resin products. Exterior parts of home appliances such as TVs, washing machines, and the like, and electronic products such as computers, mobile phones, and the like, are currently manufactured using non-coated resin. Surfaces of products made of non-coated resin can, however, be easily scratched by dust, cleaning outfits, impact, and the like, during storage, transport or usage thereof. Accordingly, there is a need to solve such problems by improving the scratch resistance of plastic resins and developing an evaluation method which can exactly estimate scratch resistance of a resin injection-molded product, film, or similar product.

Generally current methods for evaluating scratch resistance of a resin injection-molded product, film, coating, and the like include 1) a pencil hardness test, 2) a scratch evaluation method using a diamond or sapphire chip and 3) a rubbing test.

The pencil hardness test is a method for evaluating scratch resistance which uses pencil leads with different degrees of hardness, as shown below, to scratch a surface of a resin. The pencil hardness test determines whether a resin passes or fails the test ("Pass/Fail") on the basis of visual estimation.

$$6B - 5B - 4B - 3B - 2B - B - HB -$$
$$F - H - 2H - 3H - 4H - 5H - 6H$$
Softer ← -------------- → Harder In the pencil hardness test, evaluation results of scratch resistance are affected by test conditions such as temperature and humidity, and the state of the pencil leads used for the test. Additionally, reproducibility of the pencil hardness test is low and the evaluation results vary from person to person, because determining whether a scratch is produced on a test sample is visually determined and producing the scratch with a constant load is difficult. Moreover, since measurement results are represented as an attribute data such as Pass/Fail, the pencil hardness tests can not provide quantitative test results. Further, the pencil hardness test cannot discriminate differences in scratch resistances between two test samples if the two test samples have the same pencil hardness grade.

The pencil hardness test is a system that statistically determines Pass/Fail. In particular, the pencil hardness test starts with the hardest pencil and continues using progressively softer pencils until the hardest pencil that does not scratch the test sample has been established. Therefore, the pencil hardness test takes a long time due to the repeated measurements.

In the scratch evaluation method using the diamond or sapphire chip, a diamond or sapphire chip is used to scratch a surface of a test sample with a load which progressively increases up to about 1 N to about 5 N. Scratch resistance of the test sample is evaluated based on a critical load at which the scratch occurs.

As in the pencil hardness test, in the scratch evaluation method using the diamond or sapphire chip, the critical load is visually checked, and the scratch resistance is evaluated based on Pass/Fail criterion. Therefore, test results of this method are difficult to objectify and quantify.

A taber test and a rubbing test are mainly used as the rubbing test.

In the taber test, the original weight of a test sample is measured. The test sample is then brought into contact with an abrasion wheel under a load of about 1000 g and allowed to spin for about 500 revolutions. After spinning, a final weight of the test sample is taken, and the weight loss of the test sample is calculated. Wear resistance and scratch resistance are evaluated using the weight loss. During the taber test, surface melting of the test sample and adhesion between the test sample and the abrasion wheel can cause errors, and thus discrimination of the taber test falls.

In the rubbing test, an abrader repeatedly scratches a surface of a test sample with a constant load at a constant rate, and the scratches formed on the surface are visually evaluated.

As described above, conventional methods for evaluating scratch resistance determine whether a sample passes or fails based on visual observation of a scratch produced on a surface of a test sample or evaluate scratch resistance based on weight loss of the test sample.

In such conventional methods, scratch resistance of the same test sample tends to vary from measurer to measurer and it is difficult to reproduce the tests even for the same measurer. Therefore, an evaluation method based not on visual evaluation but quantitative data is strongly required for reliable and reproducible evaluation of scratch resistance.

Additionally, when the scratch resistance of a film or coating is evaluated using conventional methods, it is difficult to generate a scratch on the film or coating, and thus the evaluation of the scratch resistance may not be accurate.

SUMMARY OF THE INVENTION

One aspect of the present invention provides a method for evaluating scratch resistance of a plastic resin. In the method of the present invention, a surface of a test sample of the plastic resin is scratched using a scratch apparatus to form a scratch of the surface of the sample having a scratch profile. The scratch profile is measured by scanning the scratched surface of the test sample with a surface profile analysis apparatus. A scratch resistance evaluation index is then determined based on the measured scratch profile and is used to evaluate the scratch resistance of the test sample.

In some embodiments, the scratch apparatus scratches the surface of the test sample with a load ranging from about 1 g to about 3,000 g and at a rate less than or equal to about 300 mm/min.

In some embodiments, the surface profile analysis apparatus is a contact type or a non-contact type surface profile analysis apparatus.

In some embodiments, the scratch resistance evaluation index comprises (a) a scratch width, (b) a scratch depth, (c) a maximum hill-to-valley range and (d) a profile area.

The method of the invention for evaluating scratch resistance of a plastic resin can have excellent reliability and reproducibility, can reduce errors such as caused by measurers and measuring conditions, can offer easy measurement, can decrease measurement time, and can be applicable for all plastic resins, regardless of the type and/or manufacturing method. The method further can provide a quantitative scratch resistance evaluation index by using a scratch apparatus and a surface profile analysis apparatus.

The present invention is described more fully hereinafter with reference to the accompanying drawings.

DETAILED DESCRIPTION OF THE INVENTION

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

A method for evaluating scratch resistance of a plastic resin comprises scratching a surface of a test sample of the plastic resin using a scratch apparatus to form a scratch on the surface of the resin having a scratch profile; measuring the scratch profile by scanning the scratched surface of the test sample with a surface profile analysis apparatus; and determining or calculating a scratch resistance evaluation index based on the measured scratch profile to evaluate the scratch resistance of the test sample.

Figure 1:
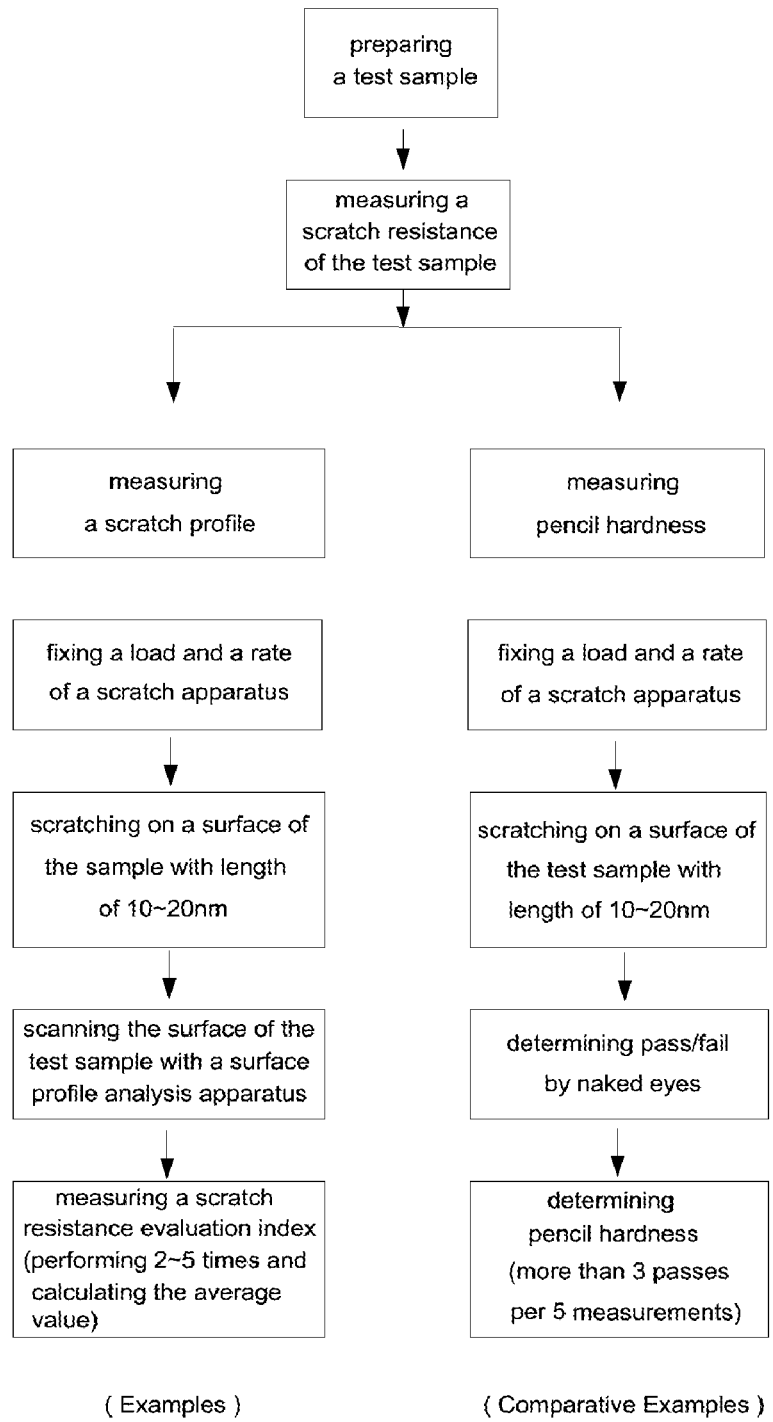
FIG. 1 is a flow chart illustrating a method of the present invention and a conventional method.
Figure 2:
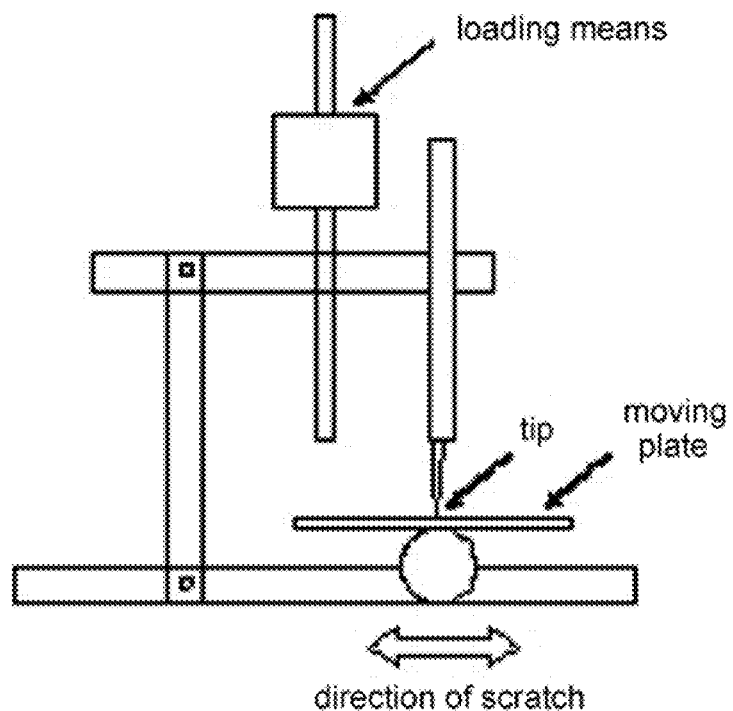
FIG. 2 is a drawing illustrating a scratch apparatus used in some embodiments of the present invention.

FIG. 1 is a flow chart comparing a method of the present invention with a conventional method. FIG. 2 is a drawing illustrating a scratch apparatus used in some embodiments of the present invention.

Referring to FIG. 2, the scratch apparatus comprises a moving plate on which the test sample is loaded, a tip for scratching the surface of the test sample on the moving plate with a load and at a rate and a loading means for applying the load to the tip. The scratch apparatus may scratch the surface of the test sample with a load ranging from about 1 g to about 3,000 g, for example about 50 g to about 2,000 g, and at a rate less than or equal to about 300 mm/min., for example from about 10 mm/min to about 200 mm/min. The load may be controlled, for example, by balance weights of about 50, 100, 200, 500, or 1,000 g.

The material of the tip may be a metal, a mineral material or an inorganic material, which are harder than the test sample to be scratched. An end portion of the tip may have a spherical, cylindrical, conical or polypyramidal shape.

When the end portion of the tip has a spherical or cylindrical shape, the diameter of the end portion of the tip may range from about 0.1 mm to about 2 mm. When the end portion of the tip has a conical or polypyramidal shape, the largest cross-section of the end portion of the tip may have a diameter or a major axis ranging from about 0.1 mm to about 3.5 mm, and an angle of the end portion of the tip may range from about 10° to about 60°.

The tip is brought into contact with the surface of the test sample and scratches the surface of the test sample with the aforementioned load and at the aforementioned rate to produce the scratch on the surface of the test sample. The scratch will have a scratch profile including certain dimensions or components, as described in more detail herein. The angle between the tip and the surface of the test sample may be freely adjusted. The angle between the tip and the surface of the test sample may range from about 30° to about 90°.

After the scratch is produced on the surface of the test sample as previously described, the scratch profile is measured by scanning the scratched surface of the test sample with a surface profile analysis apparatus.

The surface profile analysis apparatus may be a contact type or non-contact type surface profile analysis apparatus.

The contact type surface profile analysis apparatus may be a surface profile analyzer which scans the scratched surface of the test sample with a metal stylus tip having a diameter ranging from about 0.5 μm to about 2 μm and measures the scratch profile. The non-contact type surface profile analysis apparatus may be an optical analyzer. Examples of the optical analyzer may include a three-dimensional microscope, an optical analyzer (AFM), and the like.

In some embodiments of the present invention, the scratch profile is measured using a contact type surface profile analysis apparatus, Model No. XP-1, available from AMBIOS technology.

The surface profile analysis apparatus may have a horizontal scan length ranging from about 1 mm to about 30 mm, a vertical scan length ranging from about 1 μm to about 100 μm and sub-nanoscale resolution. Vertical resolution of the surface profile analysis apparatus may range from about 1 Å to about 30 Å. In particular, the vertical resolution may be about 1 Å up to about 10 μm and about 15 Å up to about 100 μm.

After the scratch profile is measured, a scratch resistance evaluation index is provided, based on the measured dimensions of the scratch profile, and the scratch resistance of the test sample is evaluated based on the scratch resistance evaluation index.

Figure 3:
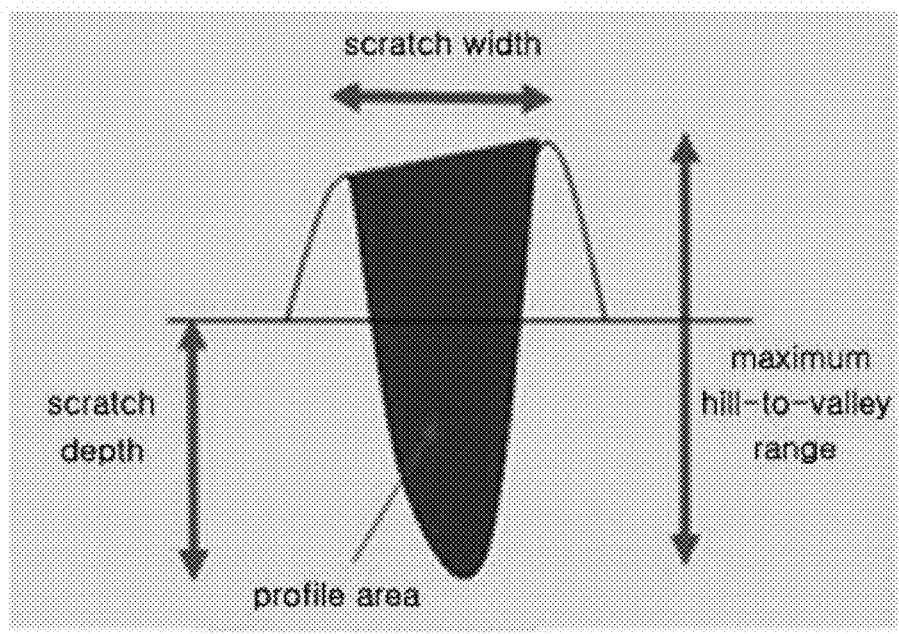
FIG. 3 is a diagram illustrating a scratch resistance evaluation index.

In this regards, measurement of the scratch profile can provide a quantitative analysis of the scratch on the surface of the resin. In exemplary embodiments, the scratch profile can include dimensions of the scratch such as (a) scratch width, (b) scratch depth, (c) maximum hill-to-valley range and (d) profile area. In this embodiment of the invention, the scratch resistance evaluation index, which is determined from the measured dimensions of the scratch profile, accordingly also comprises (a) a scratch width, (b) a scratch depth, (c) a maximum hill-to-valley range and (d) a profile area, which are illustrated in detail in FIG. 3.

The scratch resistance evaluation index accordingly may be quantified. Ranges of each of the scratch resistance evaluation index are as follows:

(a) the scratch width may range from about 0 μm to about 1,400 μm, for example about 0 μm to about 1,000 μm, and as another example about 0 μm to about 700 μm, (b) the scratch depth may range from about 0 μm to about 300 μm, for example about 0 μm to about 100 μm, and as another example about 0 μm to about 50 μm, (c) the maximum hill-to-valley range may range from about 0 μm to about 500 μm, for example about 0 μm to about 100 μm, and as another example about 0 μm to about 50 μm, (d) the profile area may range from about 0 μm$^2$ to about 155,000 μm$^2$, for example about 0 μm$^2$ to about 30,000 μm$^2$, and as another example about 0 μm$^2$ to about 10,000 μm$^2$.

The dimensions of the scratch profile may be measured more than one time, for example at least 2 and up to 5 times, or more, and the scratch resistance evaluation index may be based on an average of the multiple measurements of the scratch profile components or dimensions. The scratch resistance of the test sample is then evaluated based on the average of the measurements of the scratch resistance evaluation index.

As each component of the scratch resistance evaluation index decreases, the scratch resistance of the test sample increases. In particular, the test sample of the plastic resin is determined to be more scratch resistant when the scratch width, the scratch depth, the maximum hill-to-valley range and the profile area decrease.

There is no limitation to the plastic resin to which the method of the present invention is applied. Examples of the plastic resin may include an injection-molded product of thermoplastic or thermosetting resin, an extrusion-molded product of thermoplastic or thermosetting resin, a film of thermoplastic or thermosetting resin, a coating of thermoplastic or thermosetting resin, and the like.

The test sample may have a plane surface, and there is no limitation to a shape of the test sample. When the test sample is in a shape of a circle, a diameter of the test sample may be less than or equal to about 140 mm. When the test sample is not in a shape of a circle, a major axis of the test sample may be less than or equal to 140 mm.

When the test sample is an injection-molded product, the thickness of the test sample may range from about 0.5 mm to about 4 mm. When the test sample is a film or coating, the minimum thickness of the test sample may be more than or equal to about 1 μm, and the sum of thicknesses of the test sample and the moving plate may range from about 0.5 μm to about 4 μm.

According to the method of the present invention, a scratch profile on a surface of a test sample may be directly measured irrespective of color or gloss of the test sample. Therefore, there is no limitation to the color of the test sample to be tested, and the method of the present invention may be applicable for any of a transparent test sample, opaque color test sample and test sample having a pattern.

Additionally, if a test sample only has the aforementioned thickness, the method of the present invention may be applicable for any of an injection-molded product, a film product and a coating product, regardless of the manufacturing processes used to make the products. Accordingly, the method of the present invention may be widely used in the plastic industry.

The invention may be better understood by reference to the following examples, which are intended for the purpose of illustration and are not to be construed as in any way limiting the scope of the present invention, which is defined in the claims appended hereto.

EXAMPLES

Products manufactured by different molding processes are used as test samples for evaluating scratch resistance. In particular, (A) a plastic injection-molded test sample, (B) a plastic film test sample and (C) a coating test sample are used.

Thermoplastic test samples (A1, A2, and A3), each prepared by injection-molding three different thermoplastic resins, are used as the plastic injection-molded test sample (A).

The three different thermoplastic resins are (A1) an acrylonitrile-butadiene-styrene (ABS) copolymer resin (trade name: SD-0150, produced by Cheil Industries, Inc.), (A2) a polycarbonate (PC) resin (trade name: Panlite L-1250WP, produced by Teijin Chemicals Ltd.) and (A3) a polymethylmethacrylate (PMMA) resin (trade name: TP-100, produced by Cheil industries, Inc.).

Each of the thermoplastic test samples (A1, A2) are divided into two colors: black (BL) and an original color (NU) of the thermoplastic resin. Color of the thermoplastic test sample (A3) is transparent (TR), which is the same as polymethylmethacrylate resin.

A transparent acrylic resin film having a thickness of about 100 μm is used as the plastic film test sample (B). A slide glass is used as a substrate for fixing the plastic film test sample (B).

A test sample prepared by brush-coating a surface of a carboxylic resin substrate with a transparent acrylic resin is used as the coating test sample (C).

Scratch resistance evaluation indexes of the test samples are measured about three times and averaged. Average values of the scratch resistance evaluation indexes are shown in Table 1.

Figure 4:
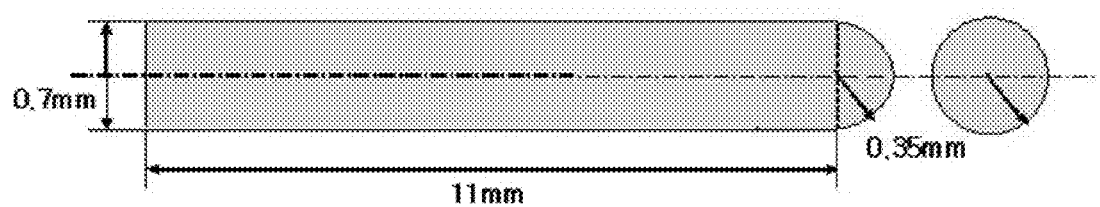
FIG. 4 is a cross-sectional view illustrating a detail shape and size of a tip which is used in the Examples.

To evaluate scratch resistances of the test samples by the method of the present invention, each surface of the test samples is scratched using a scratch apparatus, as illustrated in FIG. 2, to produce a scratch having a length ranging from about 10 mm to about 20 mm. The scratch apparatus scratched on each surface of the test samples with a constant load and at a constant rate. The constant load is about 1,000 g, and the constant rate is about 75 mm/min. The tip of the scratch apparatus is in the shape of a sphere with a diameter of about 0.7 mm. FIG. 4 illustrates in detail the shape and size of the tip.

Figure 5:
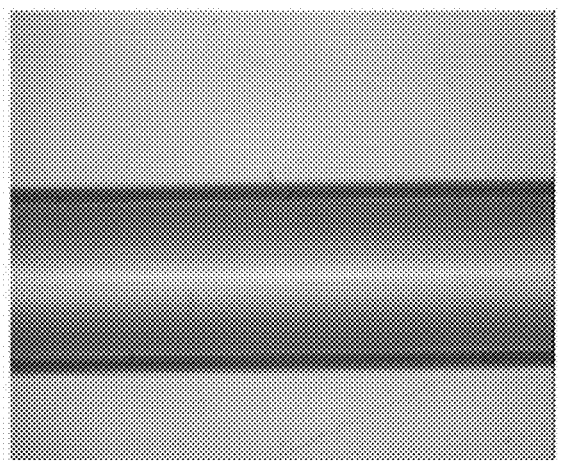
FIG. 5 is an optical microscopic image showing a scratch produced on a surface of a test sample in the Examples.

The tip is contacted with the surface of each of the test samples at an angle of about 90° and scratched on the surface of each of the test samples to form a scratch on each surface. FIG. 5 is an optical microscopic image illustrating a scratch produced on a surface of thermoplastic test sample (A1).

Figure 6:
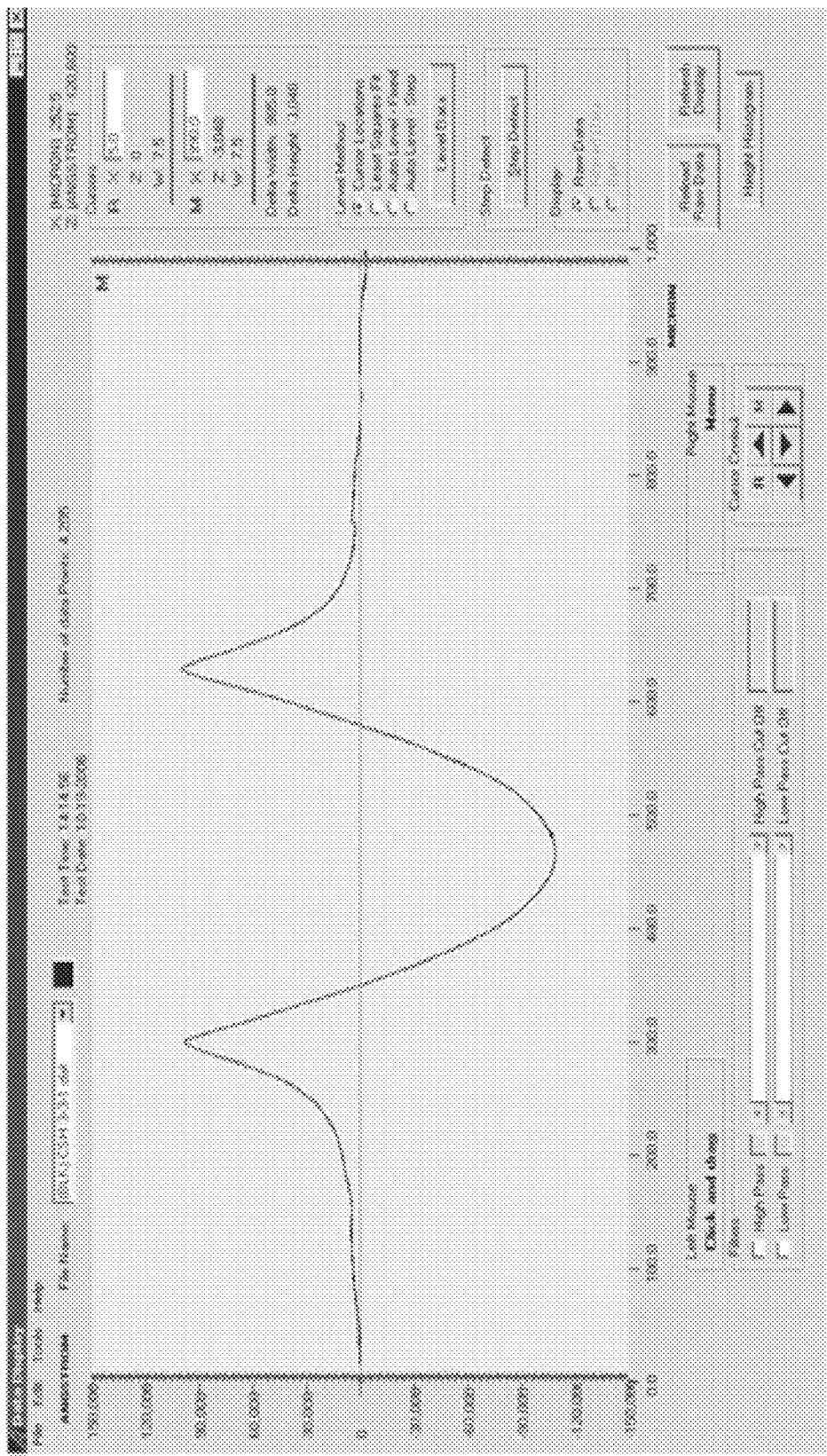
FIG. 6 is an image illustrating scratch profiles obtained by a surface profile analysis apparatus in the Examples.
Figure 6:
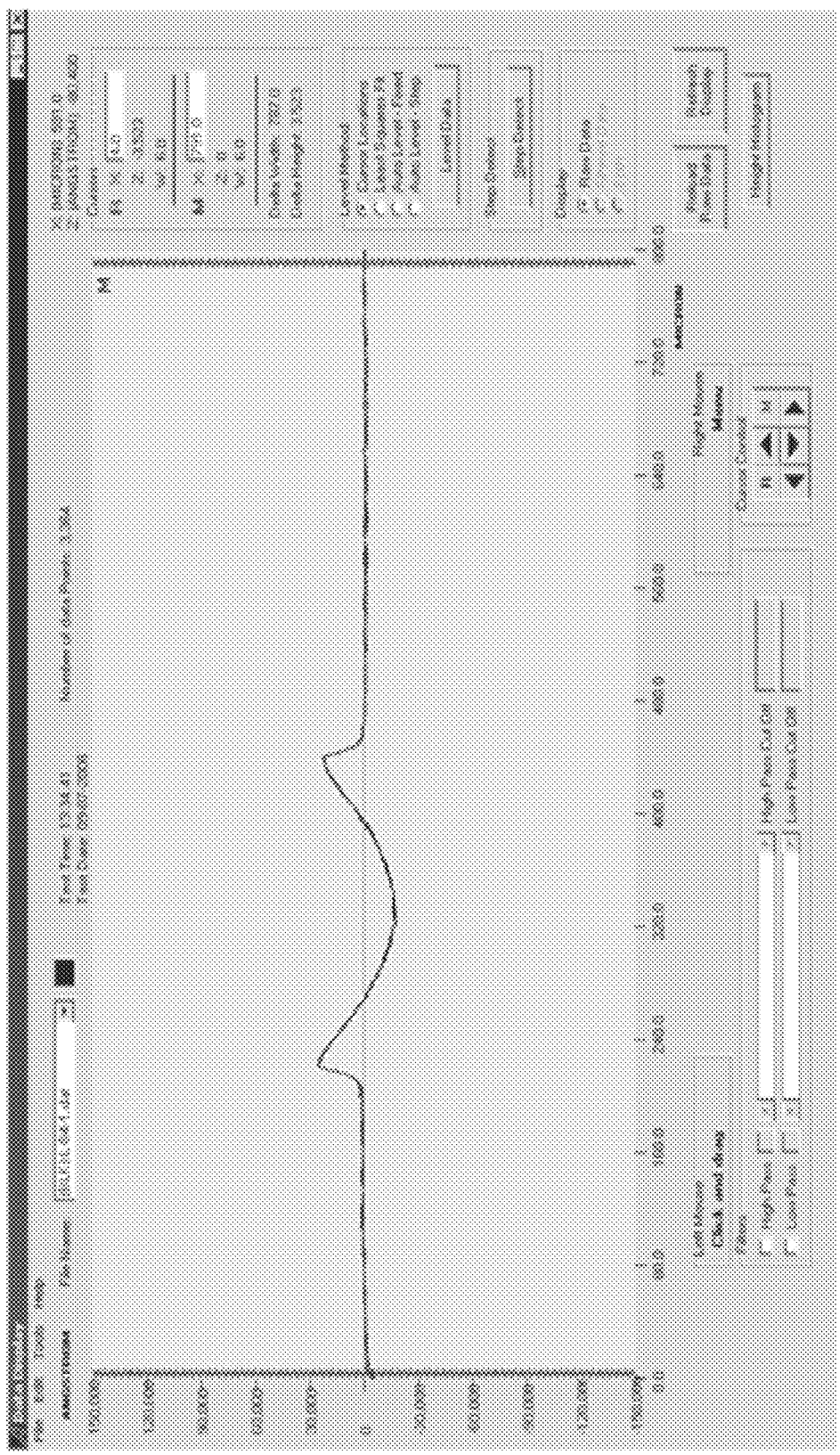

After the scratch is formed on the surface of each of the test samples, a scratch profile is measured using a contact type surface profile analysis apparatus, Model No. XP-1, available from AMBIOS technology. FIG. 6 is an image illustrating scratch profiles generated on surfaces of thermoplastic test samples (A1, A3), obtained using a surface profile analysis apparatus.

The scratch profiles can have a scratch width ranging from about 0 μm to about 1,000 μm, a scratch depth ranging from about 0 μm to about 100 μm, a maximum hill-to-valley range ranging from about 0 μm to about 100 μm and a profile area ranging from about 0 μm$^2$ to about 30,000 μm$^2$. The scratch profiles of the samples, including scratch width, scratch depth, maximum hill-to-valley range, and profile area are measured to determine the degree of scratch resistance of the samples. The results of the measurements are shown in Table 1.

Additionally, surface hardness and flexural modulus of the plastic injection-molded test sample (A) are measured.

Surface hardness is measured using a Rockwell hardness tester on a R scale according to ASTM D785. The results of the surface hardness are shown in Table 1.

Flexural modulus is measured using a test sample having a thickness of about ¼". The results of the flexural modulus are shown in Table 1. The unit of the flexural modulus is Kgf/cm$^2$.

Comparative Examples

Scratch resistances of the test samples prepared in the Examples are evaluated using a pencil hardness test which is the typical method used to evaluate scratch resistance of a plastic resin. The results of the evaluation are shown in Table 1. The pencil hardness test is performed according to ASTM D3362 or JIS K5401.

TABLE 1

| Test Sample | | Physical Properties | | Examples | | | | Comparative Examples |
|---|---|---|---|---|---|---|---|---|
| Type | Color | Surface Hardness | Flexural Modulus | Scratch Width (μm) | Scratch Depth (μm) | Maximum Hill-to-Valley Range (μm) | Profile Area (μm²) | Pencil Hardness |
| A1 | BL | 108 | 23,000 | 324 | 13.9 | 19.0 | 4,120 | 2B |
|    | NU | 108 | 23,000 | 326 | 14.0 | 19.1 | 4,350 | 2B |
| A2 | BL | 120 | 21,000 | 336 | 15.2 | 22.0 | 4,950 | 2B |
|    | NU | 120 | 21,000 | 335 | 15.0 | 21.8 | 4,900 | 2B |
| A3 | TR | 121 | 28,000 | 180 | 0.7 | 1.0 | 100 | 3H |
| B  | TR | — | — | 255 | 6.5 | 8.0 | 1,100 | H |
| C  | TR | — | — | 299 | 10.5 | 14.0 | 2,900 | HB |

As shown in Table 1, the method of the present invention, unlike the pencil hardness test which is performed by visual evaluation, provides a quantitative evaluation of scratch resistance of the plastic resin. The method of the present invention also provides reliable and reproducible test results and also reduces errors, caused by a measurer and measuring conditions, by using quantitative values which are shown in the test results of the Examples. Additionally, the method of the present invention discriminates very small differences in scratch resistance between the test samples (A1, A2). However the pencil hardness test did not discriminate any differences.

The method of the present invention can evaluate scratch resistances of color test samples and transparent test samples and does not show noticeable differences based on the color of the test samples. Thus the method of the present invention can be applicable for all plastic resins, irrespective of their color and transparency. The method of the present invention can also be applicable for films and coatings as well as injection molded products.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation, the scope of the invention being defined in the claims.

What is claimed is:

1. A method for evaluating a scratch resistance of a plastic resin, comprising:
    scratching a surface of a test sample of the plastic resin using a scratch apparatus to form a scratch on the surface having a scratch profile;
    scanning the scratched test sample with a surface profile analysis apparatus to measure the scratch profile; and
    determining a scratch resistance evaluation index based on the measured scratch profile to evaluate the scratch resistance of the test sample,
    wherein said scratch profile comprises (a) a scratch width, (b) a scratch depth, (c) a maximum hill-to-valley range and (d) a profile area, and wherein said scratch resistance evaluation index is based upon the measured scratch width, scratch depth, maximum hill-to-valley range and profile area of the scratch index.

2. The method of claim 1, wherein said scratch apparatus scratches the surface of the test sample with a load ranging from about 1 g to about 3,000 g and at a rate less than or equal to about 300 mm/min.

3. The method of claim 1, wherein said surface profile analysis apparatus is a contact type or a non-contact type surface profile analysis apparatus.

4. The method of claim 3, wherein said contact type surface profile analysis apparatus scans said scratched surface of said test sample with a metal stylus tip having a diameter ranging from about 0.5 μm to about 2 μm to measure said scratch profile.

5. The method of claim 3, wherein said non-contact type surface profile analysis apparatus is a three-dimensional microscope or an optical analyzer.

6. The method of claim 3, wherein said surface profile analysis apparatus has a horizontal scan length ranging from about 1 mm to about 30 mm, a vertical scan length ranging from about 1 μm to about 100 μm and a vertical resolution ranging from about 1 Å to about 30 Å.

7. The method of claim 1, wherein (a) said scratch width ranges from about 0 μm to about 1,400 μm, (b) said scratch depth ranges from about 0 μm to about 300 μm, (c) said maximum hill-to-valley range ranges from about 0 μm to about 500 μm and (d) said profile area ranges from about 0 μm² to about 155,000 μm².

8. The method of claim 1, wherein said scratch resistance is evaluated by measuring the scratch profile at least about 2 times to about 5 times, and calculating an average value of the scratch resistance evaluation index.

* * * * *